United States Patent [19]

Grison et al.

[11] Patent Number: 5,231,219
[45] Date of Patent: Jul. 27, 1993

[54] PROCESS FOR THE PREPARATION OF α-FLUOROACRYLATES

[75] Inventors: Claude Grison, Vandoeuvre les Nancy; Nathalie Boulliung, Nancy; Philippe Coutrot, Saulxures les Nancy, all of France

[73] Assignee: Elf Atochem S.A., Paris La Defense, France

[21] Appl. No.: 906,833

[22] Filed: Jul. 2, 1992

[30] Foreign Application Priority Data

Jul. 2, 1991 [FR] France .................. 91 08220

[51] Int. Cl.⁵ .................................. C07C 67/00
[52] U.S. Cl. .................................. 560/210
[58] Field of Search ........................ 560/210

[56] References Cited

PUBLICATIONS

Etemad-Moghadam et al., "Synthese stereoselective d'esters α,β-ethyleniques α-fluores E par reaction de Wittig-Horner a partir du diethyl phosphono α-fluoroacetate de methyle Etude comparative avec le diphenyl phosphonoxy α-fluoroacetate de methyle," Bulletin de la Societe Chimique de France, No. 3, May-Jun. 1985, pp. 448–454.

Primary Examiner—Paul J. Killos
Attorney, Agent, or Firm—Millen, White, Zelano & Branican

[57] ABSTRACT

Process for the manufacture of α-fluoroacrylates of general formula:

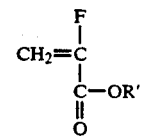

with R' alkyl, aryl or cycloalkyl, according to which source of formalin, consisting of paraformaldehyde is reacted with an α-fluorophosphonoacetate in aqueous medium in the presence of a salt of a weak inorganic acid.

12 Claims, No Drawings

PROCESS FOR THE PREPARATION OF α-FLUOROACRYLATES

The present invention relates to a process for the preparation of α-fluoroacrylates; its subject is more particularly the development of a new process for the preparation of α-fluoroacrylates which makes it possible to obtain fluorinated products of high purity in high yields while using a method of manufacture which is easy and inexpensive to implement.

Acrylic and methacrylic monomers are compounds which have been widely studied and developed in industry because of their reactivity. This reactivity makes it possible to carry out many chemical reactions, in particular to carry out various polymerisation and copolymerisation reactions resulting in materials whose applications vary very widely. Thus, for example, polymethacrylates manufactured from various acrylates or methacrylates and especially polymethyl methacrylate or PMMA as well as certain materials manufactured from various acrylates or methacrylates are particularly interesting products because of their optical and mechanical properties. They are employed, for example, in the motor industry and in the aircraft industry for the manufacture of windscreens, windows and cockpit canopies. However, their poor thermal behaviour and their poor resistance to chemical agents restrict their field of application to some extent, for example in the supersonic aviation sector. Because of this, new acrylic products which have special chemical structures have been developed in recent years.

In particular, a number of fluoroacrylic derivatives, especially α-fluoroacrylic esters have formed the subject of many studies. These α-fluoroacrylic esters correspond to the general formula

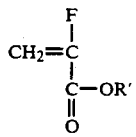

in which R' is an alkyl radical and in most cases a methyl or ethyl radical, or an aryl radical, especially a phenyl radical.

Thus, the prior art describes the preparation of α-fluoroacrylates from dihalopropanes in a two-stage reaction comprising a treatment with a mixture of $HNO_3$ and HF followed by a dehalogenation with Zn in sulphuric medium (European Application 415,214) or by a treatment of various acrylic esters with fluorine (European Application 383,128), or from a halide of α-fluoroacrylic acid, T. Nguyen and C. Wakselman, J. Org. Chem. 54, 5640 (1989) or from derivatives of the 2,2-difluoro-1-methylcyclopropane type (European Application 398,061) or from α-fluoroacrolein, H. Molines, T. Nguyen and C. Wakselman, Synthesis, 755 (1985), or by treatment of the enolate of a diethyl fluorooxaloacetate with paraformaldehyde, E. D. Bergmann and I. Shahak, J. Chem. Soc. 4033 (1961), or in four stages from vinyl ethyl ether in an overall yield of 40%, T. Nguyen, H. Molines and C. Wakselman, Synthese Comm. 15,925 (1985) or, again, in three stages from 2,2,3,3-tetrafluoro-1-propanol in an overall yield of 40%, A. Thenappan and D.3. Burton, Tetr. Letters 30, 5571 (1989).

The prior art also describes the preparation of ethyl α-fluoroacrylate from ethyl α-fluorophosphonoacetate and ethyl formate by combined action of butyllithium and of diisobutylaluminium hydride in ether at low temperatures, A. Thenappan and D.3. Burton, Journal of Fluorine Chemistry, 48, 153 (1990) and J. Org. Chem. 55, 4639 (1990) as well as the synthesis of various substituted α-fluoroacrylates corresponding to the general formula XYC=CF—COOR in which CXY is other than $CH_2$, by condensation of an -fluorophosphonoacetate with various aldehydes or ketones either in the presence of NaH in diethyl ether at low temperatures, H. Machleidt and R. Wessendorf, Ann. der Chem. 674,1 (1964); E. Elkik and Ch. Francesch, Bull. Soc. Chim. France, 5, 783 (1985) or by reaction with butyllithium in THF at −70° C., G. E. Mogmadam and J. Seyden-Penne, Bull. Soc. Chim. France, 3, 448 (1985); Ph. Coutrot and C. Grison, Journal Organomet. Chem. 1, 332 (1987).

All these processes exhibit in various degrees the disadvantage either of requiring the use of reactants which are costly or tricky to handle, or of operation under conditions which are difficult to extrapolate to an industrial scale, or of resulting in mediocre yields which do not exceed 60% in the best of cases.

There is therefore a perceived need to have available processes permitting the use of reactants which are easy to handle and inexpensive with a view to obtaining α-fluoroacrylic esters of good quality in good yields.

The present invention relates to a process for the preparation of -fluoroacrylates of the general formula I:

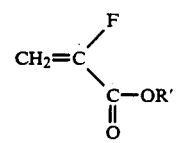

in which R' is a linear or branched alkyl radical containing from 1 to 12 carbon atoms or a mono- or polycondensed cycloalkyl radical containing from 3 to 10 carbon atoms, an aryl radical containing from 6 to 10 carbon atoms, unsubstituted or substituted by one or more alkyl groups and optionally containing one or more heteroatoms such as S, N, O or P, according to which the process comprises two stages: the synthesis of an α-fluorophosphonoacetate in a known manner in a first stage and the obtaining of the α-fluoroacrylate prepared in the second stage by condensation of the α-fluorophosphonoacetate with an aldehyde, characterised in that the aldehyde employed is formaldehyde and that it is used as such or in the form of paraformaldehyde, the condensation reaction being carried out in an aqueous medium in the presence of a weak inorganic base.

It has been found that the use of such a process makes it possible to operate under relatively mild conditions and results in good yields of the acrylates of general formula I. In addition, the operating conditions according to the process of the invention do not require the use of costly organometallic reactants which, furthermore, require constraining recovery operations.

One of the particular forms of the process of the present invention consists in employing paraformaldehyde in aqueous solution as a source of formaldehyde. According to the invention, paraformaldehyde is depolymerised in the reaction mixture by any means known to a person skilled in the art, for example in the presence of phosphoric acid at the time of the condensation reaction with the α-fluorophosphonoacetate. It has been found, in fact, that the depolymerisation of paraformaldehyde at the time of use makes it possible subsequently to carry out a good condensation with the α-fluorophosphonoacetate. According to the invention 0.33 to 10 moles of paraformaldehyde are used per 1 mole of α-fluorophosphonoacetate.

According to another characteristic of the process of the invention the condensation of formaldehyde with the α-fluorophosphonoacetate is carried out in the presence of a weak base. According to the invention the base is preferably chosen from a salt of a weak inorganic acid; in particular salts of carbonic acid, the metal being an alkali or alkaline-earth metal. According to the invention potassium carbonate is preferably employed. The quantity of the salt of a weak acid which is employed is between 1 and 5 moles per 1 mole of the α-fluorophosphonoacetate.

According to the invention an α-fluorophosphonoacetate is manufactured in a known manner in a first stage by a so-called Arbusov reaction and ethyl α-fluorodiethylphosphonoacetate such as II can be obtained, for example, by reaction of ethyl bromofluoroacetate with triethyl phosphate according to the reaction:

(RO)₃P + CHFBr COOR ⟶

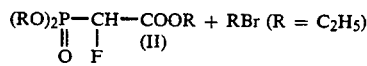

(RO)₂P—CH—COOR + RBr (R = C₂H₅)
∥    |
O    F           (II)

It is also possible to prepare, a known manner, various alkyl α-fluorophosphonoacetates by transesterification of an α-fluorophosphonoacetate such as II, described above, using various alcohols in the presence of catalysts such as, for example, a titanium tetraalkanoate Ti(OR)₄. It is also possible, in a known manner, to obtain aryl α-fluorophosphonoacetates from a 2-dialkylphosphonofluoroacetic acid. The latter is converted into acid chloride, which is then subjected to a reaction with a phenol in the presence of a base such as pyridine or a tertiary amine or of an alkali metal alcoholate.

The following examples illustrate the present invention.

All the quantities are expressed in parts by weight.

EXAMPLE 1 a) Preparation of ethyl 2-diethylohosohonofluoroacetate (II)

10 parts of ethyl bromofluoroacetate are introduced into a reactor comprising a distillation column and fitted with a heater, and are then preheated with stirring to 70° C. 9.8 parts of triethyl phosphate are then added in small quantities so that the ethyl bromide formed distills as the reaction progresses. The temperature of the reaction mixture is gradually brought to 140° C. and stirring is continued for 4 hours at this temperature. After cooling the reaction mixture 11.13 parts of phosphonate (II) are collected by vacuum distillation. B.p.₀.₆ ₘₘ: 112°, yld: 85%.

The NMR spectrum of this product is consistent with the expected structure.

b) Preparation of ethyl α-fluoroacrylate

The following are introduced into a reactor fitted with a stirrer and a heater:

3.35 parts of paraformaldehyde
0.126 parts of a 1N solution of phosphoric acid
2.5 parts of water.

The mixture is heated to 90° C. for 1 hour 30 minutes and this results in a clear solution of formaldehyde. 2.23 parts of ethyl 2-diethylphosphono-2-fluoroacetate are then added to this solution. The reaction mixture is stirred for 30 minutes at room temperature. A solution of potassium carbonate consisting of 10 millimoles of potassium carbonate, that is 1.4 parts in 3 parts of water, is then added dropwise. The addition of this alkaline solution results in a rise in temperature of the reaction mixture, which changes from 20° C. to 40° C. The mixture is then stirred for 15 minutes at this temperature and is then returned to room temperature with the aid of an iced water bath. 6 parts of ether and 4 parts of an aqueous solution saturated with sodium chloride are then added to the reaction mixture. After extraction with ether the organic phase is dried over magnesium sulphate. After evaporation of the solvent 0.9 parts of ethyl α-fluoroacrylate are collected, which corresponds to an 82% yield. The infrared and nuclear magnetic resonance spectra allow the structure of the product obtained to be confirmed.

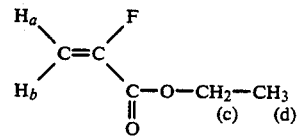

- Infrared spectrum: —C— = 1745 cm⁻¹
                    ∥
                    O $>$C=C$<$  1650 cm⁻¹

NMR spectrum:

Chemical shift (δ) (CH₃) (d) : 1.36 ppm (CH₂) (c) : 4.31 ppm (CH) (a) : 5.29 ppm Coupling constant (J) (H₁–F) : 13 hertz (Hₐ–H_b) : 1.5 hertz (H_b–F) : 42 hertz (H_b–Hₐ) 1.5 hertz

EXAMPLE 2 a) Preparation of n-butyl 2-diisopropylohosphono-2-fluoroacetate

Methyl 2-diisopropylphosphono-2-fluoroacetate is prepared according to the procedure described in Example 1.

This product is then subjected to a transesterification reaction using n-butanol. 1.49 parts of methyl 2-diisopropylphosphono-2-fluoroacetate, 0.43 parts of n-butanol, 0.22 parts of titanium tetrabutanoate and 30 parts of benzene are introduced into a reactor fitted with a heater, a stirrer and a reflux apparatus. The mixture is refluxed for 24 hours. After evaporation of the benzene 1.55 parts of butyl 2-diisopropylphosphono-2-fluoroacetate are collected, which corresponds to a 90% yield. The NMR and infrared spectra make it possible to confirm the structure of the product obtained, which has the following structure:

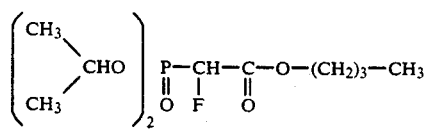

b) Preparation of butyl α-fluoroacrylate

This ester is prepared by applying the same operating procedure as that described in Example 1 (b) but starting with n-butyl 2-diisopropylphosphono-2-fluoroacetate. After treatment n-butyl α-fluoroacrylate is collected in an 80% yield.

The infrared and NMR spectra make it possible to confirm the structure of the ester obtained:

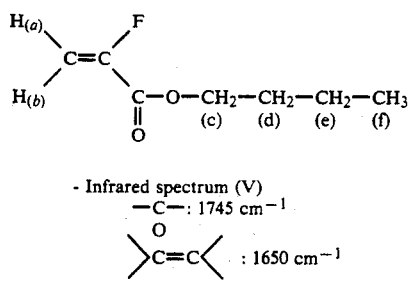

- Infrared spectrum (V)
  $-\underset{\underset{O}{\|}}{C}-$ : 1745 cm$^{-1}$ $\rangle C=C\langle$ : 1650 cm$^{-1}$ NMR spectrum Chemical shift (δ) (CH$_3$) : 0.95 ppm (CH$_2$).: 1.30–1.51 ppm (CH$_2$)$_d$ : 1.71 ppm (CH$_2$)$_c$ : 4 23 ppm (H)$_a$ : 5.30 ppm Coupling constant (J) (H$_a$–F) : 12.5 hertz (H$_a$–H$_b$) 1.5 hertz (H$_b$–F) : 43 hertz

EXAMPLE 3

The procedure of Example 1b is repeated, but starting with methyl 2-diisopropylphosphono-2-fluoroacetate as intermediate starting material.

Methyl α-fluoroacrylate is collected in a 70% yield. The infrared and NMR spectra make it possible to confirm the structure of the product

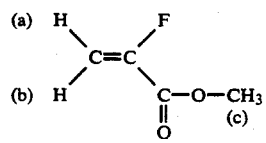

- Infrared spectrum

Infrared spectrum (C=O) : 1745 cm$^{-1}$ (C=C) : 1650 cm$^{-1}$

NMR spectrum

Chemical shift (δ) (CH$_3$) : 3.85 ppm (H)$_a$ : 5.35 ppm

Coupling constant (J) J H$_a$–F : 12.5 hertz J H$_a$–H$_b$ : 1.5 hertz J H$_b$–F : 43 hertz J H$_b$–H$_a$ : 1.5 hertz

We claim:

1. In a process for the manufacture of an α-fluoroacrylate of general formula

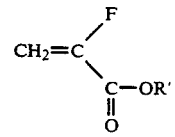

in which R, is a linear or branched alkyl radical containing from 1 to 12 carbon atoms, a mono- or polycondensed cycloalkyl radical containing from 3 to 10 carbon atoms, or an aryl radical containing from 6 to 10 carbon atoms, unsubstituted or substituted by one or more alkyl groups and optionally containing one or more heteroatoms such as S, N, O or P, said process comprising two stages: preparing an α-fluorophosphonoacetate in a first stage and preparing the α-fluoroacrylate in a second stage by condensation of the α-fluorophosphonoacetate with an aldehyde, the improvement wherein the aldehyde employed is formaldehyde in the form of free formaldehyde or paraformaldehyde, the condensation reaction being carried out in an aqueous medium in the presence of a weak inorganic base.

2. A process according to claim 1, wherein the paraformaldehyde is depolymerised in the reaction mixture at the time of the condensation reaction with the α-fluorophosphonoacetate.

3. A process according to claim 1, wherein the condensation reaction is carried out in the presence of a weak base chosen from a salt of a weak inorganic acid.

4. A process according to claim 3, wherein the salt is potassium carbonate.

5. A process according to claim 2, wherein the condensation reaction is carried out in the presence of a weak base chosen from a salt of a weak inorganic acid.

6. A process according to claim 5, wherein the salt is potassium carbonate.

7. In a process for the manufacture of an α-fluoroacrylate of general formula I:

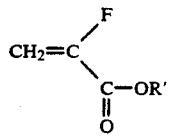

in which R, is a linear or branched alkyl radical containing from 1 to 12 carbon atoms, a mono- or polycondensed cycloalkyl radical containing from 3 to 10 carbon atoms, or an aryl radical containing from 6 to 10 carbon atoms, unsubstituted or substituted by one or more alkyl groups and optionally containing one or more heteroatoms such as S, N, O or P, said process comprising preparing the α-fluoroacrylate by condensation of an α-fluorophosphonoacetate with an aldehyde, the improvement wherein the aldehyde employed is formaldehyde in the form of free formaldehyde or paraformaldehyde, the condensation reaction being carried out in an aqueous medium in the presence of a weak inorganic base.

8. A process according to claim 7 wherein the paraformaldehyde is depolymerised in the reaction mixture at the time of the condensation reaction with the α-fluorophosphonoacetate.

9. A process according to claim 7 wherein the condensation reaction is carried out in the presence of a weak base chosen from a salt of a weak inorganic acid.

10. A process according to claim 9, wherein the salt is potassium carbonate.

11. A process according to claim 8, wherein the condensation reaction is carried out in the presence of a weak base chosen from a salt of a weak inorganic acid.

12. A process according to claim 11, wherein the salt is potassium carbonate.

* * * * *